(12) United States Patent
Jewell

(10) Patent No.: US 8,668,922 B2
(45) Date of Patent: Mar. 11, 2014

(54) COMBINATION OF LIMITED NUTRIENTS AND ENHANCED DIETARY ANTIOXIDANTS TO IMPART IMPROVED KIDNEY HEALTH

(75) Inventor: Dennis E. Jewell, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 285 days.

(21) Appl. No.: 12/245,982

(22) Filed: Oct. 6, 2008

(65) Prior Publication Data

US 2009/0047361 A1 Feb. 19, 2009

Related U.S. Application Data

(62) Division of application No. 11/024,541, filed on Dec. 29, 2004.

(51) Int. Cl.
*A23K 1/17* (2006.01)
*A23K 1/165* (2006.01)

(52) U.S. Cl.
USPC ........................................................ 424/442

(58) Field of Classification Search
USPC ........................................................ 424/442
See application file for complete search history.

(56) References Cited

U.S. PATENT DOCUMENTS

| | | | |
|---|---|---|---|
| 5,723,441 A | 3/1998 | Higley et al. | |
| 5,792,473 A | 8/1998 | Gergely et al. | |
| 5,851,573 A | 12/1998 | Lepine et al. | |
| 6,039,952 A | 3/2000 | Sunvold et al. | |
| 6,150,399 A | 11/2000 | Patel et al. | |
| 6,306,442 B1 | 10/2001 | Sunvold et al. | |
| 6,376,544 B2 | 4/2002 | Lowry et al. | |
| 6,447,989 B1 | 9/2002 | Comper | |
| 6,458,767 B1 | 10/2002 | Murphy-Ullrich et al. | |
| 6,492,325 B1 | 12/2002 | Cosgrove | |
| 6,589,748 B2 | 7/2003 | Comper | |
| 6,599,876 B2 | 7/2003 | Kojima | |
| 6,784,159 B2 | 8/2004 | Holub et al. | |
| 2001/0043983 A1 | 11/2001 | Hamilton | |
| 2002/0028762 A1 | 3/2002 | Kojima | |
| 2003/0060503 A1 | 3/2003 | Hamilton | |
| 2003/0105027 A1 | 6/2003 | Rosenbloom | |
| 2003/0198661 A1 | 10/2003 | Harper et al. | |
| 2004/0047896 A1 | 3/2004 | Malnoe et al. | |
| 2004/0105879 A1 | 6/2004 | Heaton et al. | |
| 2004/0137080 A1 | 7/2004 | Cremisi | |
| 2005/0026225 A1 | 2/2005 | Comper | |

FOREIGN PATENT DOCUMENTS

| | | |
|---|---|---|
| CA | 2321909 | 9/1999 |
| JP | 2002-535364 A | 10/2002 |
| JP | 2003-528050 A | 9/2003 |
| JP | 2004-519241 A | 7/2004 |

(Continued)

OTHER PUBLICATIONS

Klahr et al (Kidney International, vol. 24 (1983) pp. 579-587).*

(Continued)

*Primary Examiner* — Benjamin Packard
(74) *Attorney, Agent, or Firm* — Thomas M. Hunter

(57) ABSTRACT

This invention is directed to compositions for animal consumption (including foods, treats, etc.), particularly compositions that tend to improve kidney function, and particularly compositions that comprise enhanced antioxidants and reduced quantities of protein and/or phosphorus. This invention also is directed generally to methods for using such compositions.

4 Claims, 1 Drawing Sheet

(56) References Cited

FOREIGN PATENT DOCUMENTS

| WO | WO 01/58882 | 8/2001 |
|---|---|---|
| WO | 03061402 A2 | 7/2003 |
| WO | WO 2004/113570 | 12/2004 |

OTHER PUBLICATIONS

Chade et al (Beneficial Effects of Antioxidant Vitamins on the Stenotic Kidney, Hypertension 42 (2003) pp. 605-612).*
Jewel (Veterinary Therapeutics, vol. 1, No. 4 (2000) 264-272).*
Pober (http://www.raingoddess.com/dogfood/phos.html, accessed Dec. 14, 2010).*
Markell (Waltham Focus, vol. 8 No. 2 (1998 16-22).*
Mattina, Analysis of Agricutural Feeds and Pet Foods, 1998, The Connecticut Agricultural Experiment Station, New Haven, Bulletin 956, May 1999.*
Baud et al (AJP—Renal Physiol, 1986, v251, n5, F765-F776).*
Jacob. et al. "Clinical Evaluation of Dietary Modification for Treatment of Spontaneous Chronic Renal Failure in Dogs", JAVMA (2002), pp. 1163-1170, 220:8.
Monzani, et al. "LP(A) Levels: Effects of Progressive Chronic Renal Failure and Dietary Manipulation," J of Nephrology, (1997) pp. 41-45, 10:1.
Ongajooth, et al., "Role of Lipid Peroxidation, Trace Elements and Anti-Oxidant Enzymes in Chronic Renal Disease Patients," J Med Assoc. Thai (1996) pp. 791-800.
Sudhir V, Shah, "The Role of Reactive Oxygen Metabolites in Glomerular Disease," Annu. Rev. Physiol. (1995) 57:245-62.
Hasselwander, et al. "Oxidative Stress in Chronic Renal Failure," Free Rad. Rev., (1997) 29:1-11.
Cottrell, et al., Mitochondria and Ageing, CL Nutr and Meta Care, (2000) 3:473-478.
Endraffy, ET. et al. The effects of vitamin E on tissue oxidation in nephrotoxic (anti-glomerular basement memebrane) Pediatr Nephrol (1991) 3:312-7, Abstract only.
Beckman et al. "The free radical theory of aging matures." Phys. Rev (1998) pp. 547-581 78.
Cutler, Richard G., "Antioxidants and Aging," Am. J. Clin. Nutr. (1991) pp. 373S-379S 53.
Tylicki, L., et al. "Antioxidants: A Possible Role in Kidney Protection," Kid, BL. Press. Res..(2003) pp. 303-314, 26.
Kedziora-Kornatowska. "Effect of Vitamine E and Vitamin C Supplementation on Antioxidative State and Renal Glomerular Basement Membrane Thickness in Diabetic Kidney," Nephron Exp. Nehprol, (2003) pp. e134-e143 95.
"Reperfusion injury," Source: http://en.wikipedia.org/w/index.php?oldid=471646065.
American Feed Control Officials, Incorp., Official publication, p. 220, 2003.
American Feed Control Officials, Incorp,, Official publication, pp. 126-140, 2003.
Anonymous, 2004, "Ami-Products—Ingredients" Internet Citation, Retrieved from http://ami.aminews.net/en_ingredienti.html/
Dzanis, 1997, "Selecting Nutritious Pet Foods," Division of Animal Feeds, Center for Veterinary Medicine.
Foster et al., Dog Food Standards by the AAFCO, Veterinary Services Dept. http://www.peteducation.com/article.cfm?c=2+1659+1661&aid=662, accessed Sep. 10, 2009.
Greco, 1987, "Dietary Considerations for Dogs with Chronic Renal Failure," Companion Animal Practice, 1(1):54-56, 62.
Hand, 2000, Small Animal Clinical Nutrion, 4th Edition, p. 223.
Leibetseder et al., 1991, "Effects of Medium Protein Diets in Dogs with Chronic Renal Failure," Journal of Nutrition, 121(11 Supp):S145-149.
Loghman-Adham, 1993, M. "Role of Phosphate Retention in the Progression of Renal Failure," Lab, Clin. Med., 122(1):16-26.
Milgram et al., 2002, "Landmark Discrimination Learning in the Dog: Effects of Age, an Antioxidant Fortified Food and Cognitive Strategy," Neuroscience and Biobehavioral Reviews 26:679-695.
Oota, 2004, "Supplementary Effects of Vitamin E of Patients of Kidney Disease," Vitamins (Japan) 78(10):495-512.
Otani, 1998, "Kidney Diseases and Antioxidants," Japanese J. Clin. Nutr. 92(4):381-385.
Polzin et al., 2000, "Dietary Management of Feline Chronic Renal Failure: Where Are We Now? in What Direction are We Headed?" Journal of Feline Medicine and Surgery, 2:75-82.
"Hi-Energy Dry Dog Food-Diamond Pet Foods" http://www.diamondpet.com/products/diamond/dogs/dry_food/diamond_hienergy/ retrieved online 2012, pp. 1-2.
"Metabolic Energy Requirements for Dogs (Dog Daily Calorie Calculator") http:my.cockerspaniel.com/mer.htm; 2003, pp. 1-3.
American Assoc. Feed Control Officials, 2004, Official Publication of the AAFCO, pp. 129-137.
Chen et al., 1995, "Vitamin E, Selenium, Trolox C, Ascorbic Acid Palmitate, Acetylcysteine, Coenzyme Q, β-Carotene, Canthaxanthin, and (+)-Catechin Protect Against Oxidative Damage to Kidney, Heart, Lung and Spleen," Free Radical Res. 22(2):177-186.
International Search Report and Written Opinion in International Application No. PCT/US06/014623, mailed Aug. 2, 2006.
Shah, 1995, "The Role of Reactive Oxygen Metabolites in Glomerular Disease," Annual Rev. Physiol. 57:245-262.
Yu et al., 2006, "Dietary Supplements of Vitamins E and C and β-Carotene Reduce Oxidative Stress in Cats with Renal Insufficiency," Vet. Res. Commun. 30:403-413.

* cited by examiner

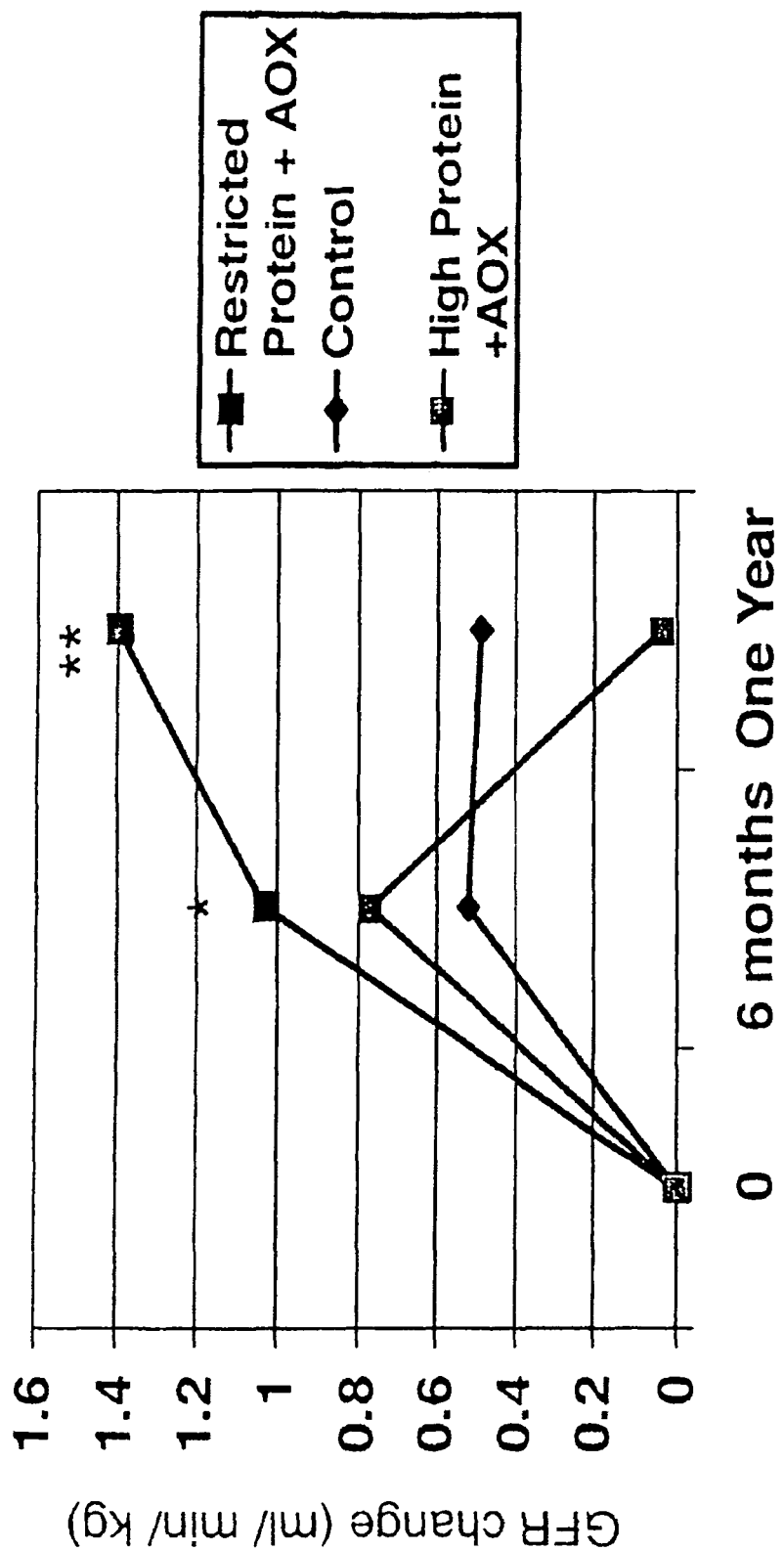

COMBINATION OF LIMITED NUTRIENTS AND ENHANCED DIETARY ANTIOXIDANTS TO IMPART IMPROVED KIDNEY HEALTH

CROSS REFERENCE TO RELATED APPLICATIONS

This application is a divisional of pending U.S. patent application Ser. No. 11/024,541, which was filed Dec. 29, 2004, which is incorporated herein by reference in its entirety.

FIELD OF THE INVENTION

This invention is directed generally to food compositions for animal consumption, particularly compositions useful to improve kidney function, as seen by reduced serum urea nitrogen and/or increased glomerular filtration rate. This invention also is directed generally to methods for using such compositions.

BACKGROUND OF THE INVENTION

It has been postulated since 1956 that the production of active oxygen species, or free radicals, pursuant to aerobic respiration, results in oxidative damage, which hastens aging and death in animals. See Beckman, K., et al., "The Free Radical Theory of Aging Matures," *Phys. Rev.*, 78: 547-581 (1998). Active oxygen species cause aging through various mechanisms, including directly damaging cellular DNA, see Cutler, R., "Antioxidants and aging", *Am. J. Clin. Nutr.*, 53: 373S-379S (1991), as well as lipids and proteins as well. See, Tylicki, L., et al. "Antioxidants: A Possible Role in Kidney Protection," *Kid. Bl. Press. Res.*, 26: 303-314 (2003). Free radicals, often produced in the mitochondria, where aerobic respiration occurs, damage mitochondrial DNA, proteins, and lipids. See, e.g., U.S. Patent App. Pub. No. U.S. 2003/0060503.

It has also been postulated that active oxygen species may play a role in causing kidney disease. See, Ongajooth L., et al. "Role of Lipid Peroxidation, Trace Elements and Antioxidant Enzymes in Chronic Renal Disease Patients," *J. Med. Assc. Thai.*, 72:791-800 (1996). Several mechanisms have been proposed to account for this increase in renal failure (see, e.g., Hasselwander, et al. "Oxidative Stress in Chronic Renal Failure," *Free Rad. Res.* 29:1-11 (1998); Shah, S., "The Role of Reactive Oxygen Metabolites in Glomerular Disease," *Annu. Rev. Physiol.*, 57:245-62 (1995)), but scientific studies to date are inconclusive regarding whether antioxidant treatment is beneficial to those with kidney disease. Some studies indicate that there is a role for various antioxidant supplementation in the protection against kidney disease. See, e.g., Kedziora-Kornatowska, "Effect of Vitamin E and Vitamin C Supplementation on Antioxidative State and Renal Glomerular Basement Membrane Thickness in Diabetic Kidney", *Nephron Exp. Nephrol.*, 95:e134-e143 (2003). Other studies note the potential pro-oxidant properties of antioxidant supplements, concluding that there is not yet enough experimental evidence to recommend antioxidant supplements to alleviate kidney disease. See, e.g., Tylicki, L., et al.

In addition to the improvement of kidney function caused by supplementation of an animal's diet with antioxidants, kidney function may also benefit from the avoidance of mineral excess. Byproducts of protein digestion and phosphorus are among the primary toxins that must be removed from the blood stream by the kidneys. Thus, by decreasing protein and/or phosphorus consumption in an animal's diet, less stress is placed upon kidney function, improving kidney health. In short, lowering the dietary intake of protein and/or phosphorus is beneficial to improving kidney function and/or lessening the progression of renal disease. See, e.g. U.S. Pat. No. 6,306,442.

Despite years of studies and developments relating to renal function and kidney disease, there continues to be a need for compositions and methods that aid in improving kidney function.

SUMMARY OF THE INVENTION

This invention is directed to compositions for animal consumption, particularly compositions that tend to improve kidney function. It is contemplated that such compositions may be suitable for use with a variety of mammalian and non-mammalian animals.

Briefly, therefore, this invention is directed, in part, to a composition for animal consumption, such as, for example, a food or treat. The composition comprises both antioxidants and a reduced amount of protein and/or phosphorus, as compared to the maximum typically recommended for a healthy animal of the same species or breed.

In one contemplated embodiment, the composition comprises about 25 to about 2,000 mg/kg vitamin C (based on dry weight of the composition).

In one contemplated embodiment, the composition comprises about 300 to about 2,000 IU/kg vitamin E (based on dry weight of the composition).

In one contemplated embodiment, the composition comprises less than about 23% protein (based on dry weight of the composition).

In one contemplated embodiment, the composition comprises less than about 0.75% phosphorus (based on dry weight of the composition).

In another contemplated embodiment, the composition is intended for consumption by a dog.

This invention also is directed to an animal treat that comprises both antioxidants and a reduced amount of protein and/or phosphorus, as compared to the maximum typically recommended for a healthy animal of the same species or breed.

This invention also is directed to methods for using such compositions to aid in improving the kidney function.

Further benefits of Applicant's invention will be apparent to one skilled in the art from reading this patent.

BRIEF DESCRIPTION OF THE FIGURES

FIG. 1 is a chart showing GFR changes over time in canines fed the three food compositions of Example 1.

DETAILED DESCRIPTION

This detailed description is intended only to acquaint others skilled in the art with Applicant's invention, its principles, and its practical application so that others skilled in the art may adapt and apply the invention in its numerous forms, as they may be best suited to the requirements of a particular use. This detailed description and its specific examples, while indicating various embodiments of this invention, are intended for purposes of illustration only. This invention, therefore, is not limited to the embodiments described in this specification, and may be variously modified.

It has been found, in accordance with this invention, that the reduction of certain nutrients in an animal's diet, c conjunction with the supplementation to that diet of certain antioxidants, can be useful to improve kidney function. Without being bound to any particular theory, Applicant be eves that is benefit may be the result of, for example, decreased toxins in the blood stream, due to the reduction of nutrients, and decreased presence of oxygen species in the blood stream, due to the introduction into the bloodstream of antioxidants.

It is contemplated that the compositions and methods of is invention may be useful for a variety of mammals, including non-human mammals such as non-human primates (e.g., monkeys, chimpanzees, etc.), companion animals (e.g., dogs, cats, equine, etc.), farm animals (e.g., goats, sheep, swine, bovine, etc.), laboratory animals (e.g., mice, rats, etc.), and wild and zoo animals (e.g., wolves, bears, deer, etc.).

In some embodiments of this invention, for example, the animal is a monogastric mammal (i.e., a mammal having a single stomach), such as, for example, a non-human primate, dog, cat, rabbit, horse, or swine.

In other embodiments of this invention, the animal is a carnivorous mammal, i.e., a meat-eating mammal.

In other embodiments of this invention, the animal is an omnivorous mammal, i.e., a mammal that eats both plants and meat.

In other embodiments of this invention, the animal is a companion animal.

In other embodiments of this invention, the animal is a cat.

In other embodiments of this invention, the animal is a dog.

In other embodiments of this invention, the animal is a rabbit.

In other embodiments of this invention, the animal is a swine.

In other embodiments of this invention, the animal is a horse.

It also is contemplated that the compositions and methods of this invention may be useful for a variety of non-mammalian animals. In some embodiments of this invention, for example, the composition is intended for consumption by a bird. Contemplated birds include, for example, companion, farm, zoo, and wild birds (e.g., including, for example, song birds, parrots, ducks, geese, chickens, turkeys, ostriches, etc.).

Enhanced or improved kidney function refers to the relative increase in the kidney's ability to remove waste or toxins from the animal's blood stream compared to an earlier point in time. Generally, as animals age, there is a decrease in the total glomerular filtration, caused by a declining ability of the kidneys to adequately filter urine. It is believed that this decrease in kidney function is caused by a decrease in nephron number and function.

Any of several blood indices may be used to determine the severity of an animal's renal disease. Among these indices is serum urea nitrogen (SUN). SU levels in the blood of an animal increase when the animal suffers from renal failure because damage to the kidney lessens the kidney's ability to adequately filter urea, a waste product. Kidney function can also be measured via the monitoring of glomerular filtration rate (GFR). The greater an animal's GERM the better the kidneys are at removing waste and, therefore, functioning. GFR can be measured in a number of ways, including the use of an iohexol clearance test. Per this test, the intended animal first fasts for twelve or more hours. Then, iohexol, a radiographic contrast agent, is injected into the blood via an intravenous catheter. At 2, 3, and 4 hours after administration of iohexol, a minimum of 4 ml of blood (at least 1.2 ml serum) is obtained and tested. The rate at which iohexol in the blood stream is decreasing indicates the level at which the kidney is functioning. The overall functioning of the animal's kidneys can be measured via a comparison of that animal's GFR at one point in time versus the animal's GFR at a later point in time.

An "antioxidant" herein is a substance that is capable of reacting with free radicals and neutralizing them. Illustrative examples of such substances include β-carotene, selenium, coenzyme $Q_{10}$ (ubiquinone), luetin, tocotrienols, soy isoflavones, S-adenosylmethionine, glutathione, taurine, N-acetylcysteine, vitamin E, vitamin C, α-lipoic acid and L-carnitine. Examples of foods containing useful levels of one or more antioxidants include but are not limited to ginkgo biloba, green tea, broccoli, citrus pulp, grape pomace, tomato pomace, carrot spinach, and a wide variety of fruit meals and vegetable meals.

Except where the context demands otherwise, the term "vitamin E" is used generically herein to encompass any tocopherol or tocotrene compound, including any enantiomer or racemate thereof, and any mixture of such compounds, having vitamin E activity, including α-tocopherol ((+)-2,5,7,8-tetramethyl-2-(4,8,12-trimethyltridecyl)-6-chromanol), β-tocopherol ((+)-2,5,8-trimethyl-2-(4,8,12-trimethylidecyl)-6-chromanol), γ-tocopherol ((+)-2,7,8-trimethyl-2-(4,8,12-trimethyltridecyl)-6-chromanol), δ-tocopherol ((+)-8-methyl-2-(4,8,12-trimethyltridecyl)-6-chromanol), α-tocotrienol (2,5,7,8-tetramethyl-2-(4,8,12-trimethyl-3,7,11-tridecatrienyl)-6-chromanol) and β-tocotrienol (2,5,8-trimethyl-2-(4,8,12-trimethyl-3,7,11-tridecatrienyl)-6-chromanol). Vitamin E can be administered as any one or a mixture of the above compounds or in the form of various derivatives thereof such as esters, including vitamin E acetate, succinate, palmitate and the like, that exhibit vitamin E activity after ingestion by the dog. Typically vitamin E as used in the present method comprises α-tocopherol or an ester thereof.

Vitamin C can be administered as ascorbic acid, for example L-ascorbic acid, or as various derivatives thereof such as calcium phosphate salt, cholesteryl salt, and ascorbate-2-monophosphate. Salts of vitamin C include, for example, sodium salt, calcium salt, zinc salt and ferrous salt. Esters include, for example, stearate, palmitate and like derivatives. Vitamin C or a derivative thereof can be in any physical form, for example, a liquid, a semisolid, a solid, or a heat stable form that exhibits vitamin C activity after ingestion by the dog.

One or more antioxidants are present in the compositions of this invention in an amount that causes the kidney function of the intended animal to improve. Any antioxidant that can provide such enhanced kidney function can be used. For example, compositions of this invention may contain vitamin C and/or vitamin E. In general, the concentration of vitamin C, if present in the compositions of this invention, is at least about 25 mg/kg (or from about 25 to about 2,000 mg/kg, or about 40 to about 1500 mg/kg, or about 50 to about 1000 mg/kg, or about 75 to about 500 mg/kg, or about 100 to about 200 mg) based on the dry weight of the composition. In general, the concentration of vitamin E, if present in the composition of this invention, is at least about 300 IU/kg (or from about 400 to about 1700 IU/kg, or about 500 to about 1400 IU/g, or about 600 to about 1100 IU/kg, or about 700-800 IU/kg) based on the dry weight of the composition. The weight ratio of vitamin C to vitamin E (as DL-alpha-tocopheryl acetate equivalents) is about 0.2:1 to about 7:1.

To reduce the stress on the kidney of an animal with reduced kidney function, the compositions of this invention also contain a reduced amount of protein and/or phosphorus, as compared to the maximum typically recommended for a healthy animal of the same species or breed. For example, it has been recommended that the maximum be 23% of a typical dog's diet comprise protein. See, e.g., *Small Animal Clinical Nutrition*, 4th ed., p. 223 (2000). In general, the concentration of protein in the dog food compositions of this invention is less than about 23% or less than about 20%, based on the dry weight of the composition. Relatedly, it has been recommended that at least 0.75% of a typical dog's diet comprise phosphorus. See, e.g., *Small Animal Clinical Nutrition*, 4th ed., p. 223 (2000). In general, the concentration of phosphorus in the dog food compositions of this invention is less than about 0.75%, based on the dry weight of the composition. The concentration of phosphorus in the compositions of this invention may also be less than about 0.60%, based on the dry weight of the composition. The concentrations of phosphorus in the compositions of this invention may also be less than about 0.50%, based on the dry weight of the composition. The weight ratio of protein to phosphorus is about 17:1 to about 110:1. The weight ratio of protein to antioxidants is about 410:1 to about 70:1.

The antioxidants are present at concentrations that are not deleterious to the intended animal's health. Thus, for example, the antioxidants are present at concentrations that do not cause undesirable toxic effects. Relatedly, while reduced, the protein and phosphorus are present in the compositions of this invention at concentrations that are sufficient to provide the intended animal sufficient dietary protein and phosphorus to maintain the overall health of the animal.

The compositions of this invention are fed to an animal for a sufficient period of time to improve kidney function as exhibited through, for example, a reduced serum nitrogen level and/or improved GFR.

Although both liquid and solid foods are contemplated, solid foods are more typical. Where the food is solid, the antioxidants may be coated on the food, incorporated into the food, or both. Contemplated foods include both dry foods or wet foods. The other components of the food and their proportions include those listed in Table 1.

TABLE 1

| Component | Proportion of the Composition (% of Dry Weight of Composition) |
| --- | --- |
| Carbohydrate (typically a nitrogen-free or essentially nitrogen-free extract) | from about 0% to about 75%, or from about 10% to about 60% |
| Fat | from about 2% to about 50%, or from about 5% to about 50%, or from about 5% to about 40% |
| Dietary fiber | from about 0% to about 40%, or from about 1% to about 20%, or from about 1% to about 5.5% |
| Nutritional balancing agents (e.g., vitamins, minerals, and trace elements) | from about 0% to about 15%, or from about 0% to about 10%, or from about 2% to about 8% |

In a contemplated embodiment, the composition is a food that comprises the following:
 (a) at least about 25 mg/kg (or from about 25 to about 2,000 mg/kg, or about 40 to about 1500 mg/kg, or about 50 to about 1000 mg/kg, or about 75 to about 500 mg/kg, or about 100 to about 200 mg/kg) vitamin C, based on the dry weight of the composition;
 (b) at least about 300 IU/kg (or from about 400 to about 1700 IU/kg, or about 500 to about 1400 IU/kg, or about 600 to about 1100 IU/kg, or about 700-800 IU/kg) vitamin E, based on the dry weight of the composition;
 (c) less than about 25% (or less than about 20%) protein, based on the dry weight of the composition; and
 (d) less than about 1.0% (or less than about 0.75%, or less than about 0.60%) phosphorus, based on the dry weight of the composition In such an embodiment, it is contemplated that the composition also may, for example, comprise at least one of the following:
 (a) from about 0% to about 75% carbohydrate,
 (b) from about 2% to about 50% fat,
 (c) from about 0% to about 40% dietary fiber, and
 (d) from about 0% to about 15% of one or more nutritional balancing agents.

Specific amounts for each component in a composition will depend on a variety of factors including, for example, the species of animal consuming the composition; the particular components included in the composition; the age, weight, general health, sex, and diet of the animal; the animal's consumption rate; the type of composition condition(s) being treated; and the like. Thus, the component amounts may vary widely, and may even deviate from the proportions set forth in this patent.

It is contemplated that the protein in the compositions of the present invention may be supplied by a variety sources, including, plant sources, animals sources, or both. Animal sources include, for example, meat, meat by-products, dairy, eggs, etc. Meats include, for example, the flesh of poultry; fish; and mammals (e.g., cattle, swine, sheep, goats, and the like). Meat by-products include, for example, lungs, kidneys, brain, livers, and stomachs and intestines (it is best if they are freed of essentially all or all their contents).

In some contemplated embodiments, the protein comprises meat, a meat by-product, a dairy product, or an egg product. In some such embodiments, for example, the total concentration of meat(s), meat by-product(s), dairy product(s), and egg product(s) in the composition is from about 5% to about 70% (or from about 10% to about 70%, or from about 10% to about 60%).

In some contemplated embodiments, the protein comprises meat or a meat by-product. In some such embodiments, for example, the total concentration of meat(s) and meat by-product(s) in the composition is from about 5% to about 70% (or from about 10% to about 70%, or from about 10% to about 60%).

The fat and carbohydrate in the compositions of the present invention may be supplied by a variety of sources, including, for example, meat, meat by-products, other animal or plant protein sources, grains, and mixtures thereof. Grains include, for example, wheat, corn, barley, and rice.

Fiber in the compositions of the present invention may be supplied from a variety of sources, including, for example, vegetable fiber sources such as cellulose, beet pulp, peanut hulls, and soy fiber.

Particularly in instances when the composition is an animal's food, vitamins and minerals are included in amounts required to avoid deficiency and maintain health. These amounts are readily available in the art. The National Research Council (NRC), for example, provides recommended amounts of such ingredients for farm animals. See, e.g., *Nutrient Requirements of Swine* (10th Rev. Ed., Nat'l Academy Press, Wash. D.C., 1998), *Nutrient Requirements of Poultry* (9th Rev. Ed., Nat'l Academy Press, Wash. D.C., 1994), *Nutrient Requirements of Horses* (5th Rev. Ed., Nat'l Academy Press, Wash. D.C., 1989), etc. And the American Feed Control Officials (AAFCO), for example, provides recommended amounts of such ingredients for dogs and cats. See American Feed Control Officials, Incorp., Official publication, pp. 126-140 (2003). Contemplated vitamins generally useful as food additives include, for example, vitamin A, vitamin B1, vitamin B2, vitamin B6, vitamin B12, vitamin D, vitamin H (biotin), vitamin K, folic acid, inositol, niacin, beta carotene and pantothenic acid. Contemplated minerals and trace elements generally useful as food additives include, for example, calcium, phosphorus, sodium, potassium, magnesium, copper, zinc, chloride, and iron salts.

The compositions of the present invention may further contain additives known in the art. Such additives are present in amounts that do not impair the purpose and effect provided by the invention. Examples of contemplated additives include, for example, substances that are functionally beneficial to improving kidney function, substances with a stabilizing effect, organoleptic substances, processing aids, substances that enhances palatability, coloring substances, and substances that provide nutritional benefits.

Contemplated stabilizing substances include, for example, substances that tend to increase the shelf life of the composition. Potentially suitable examples of such substances include, for example, preservatives, synergists and sequestrants, packaging gases, stabilizers, emulsifiers, thickeners, gelling agents, and humectants. Examples of emulsifiers and/or thickening agents include, for example, gelatin, cellulose ethers, starch, starch esters, starch ethers, and modified starches.

Contemplated additives for coloring, palatability, and nutritional purposes include, for example, colorants; iron oxide, sodium chloride, potassium citrate, potassium chloride, and other edible salts; vitamins, minerals; and flavoring. The amount of such additives in a composition typically is up to 5% (dry basis of the composition).

Supplements include, for example, a feed used with another feed to improve the nutritive balance or performance of the total. Contemplated supplements include compositions that are fed undiluted as a supplement to other feeds, offered free choice with other parts of an animal's ration that are separately available, or diluted and mixed with an animal's regular feed to produce a complete feed. The AAFCO, for example, provides a discussion relating to supplements in the American Feed Control Officials, Incorp. Official Publication, p. 220 (2003). Supplements may be in various forms including, for example, powders, liquids, syrups, pills, encapsulated compositions, etc.

Treats include, for example, compositions that are given to an animal to entice the animal to eat during a non-meal time. Contemplated treats for canines include, for example, dog bones. Treats may be nutritional, wherein the composition comprises one or more nutrients, and may, for example, have a composition as described above for food. Non-nutritional treats encompass any other treats that are non-toxic.

The antioxidants of this invention may be incorporated into the composition during the processing of the formulation, such as during and/or after mixing of other components of the composition. Distribution of these components into the composition can be accomplished by conventional means.

Compositions of the present invention (particularly foods) can be prepared in a canned or wet form using conventional pet food processes. In one contemplated embodiment, ground animal (e.g., mammal, poultry, and/or fish) proteinaceous tissues are mixed with the other ingredients, including fish oils, cereal grains, other nutritionally balancing ingredients, special purpose additives (e.g., vitamin and mineral mixtures, inorganic salts, cellulose and beet pulp, bulking agents, and the like); and water that sufficient for processing is also added. These ingredients are mixed in a vessel suitable for heating while blending the components. Heating of the mixture may be effected using any suitable manner, such as, for example, by direct steam injection or by using a vessel fitted with a heat exchanger. Following the addition of the last ingredient, the mixture is heated to a temperature range of from about 50° F. to about 212° F. Temperatures outside this range are acceptable, but may be commercially impractical without use of other processing aids. When heated to the appropriate temperature, the material will typically be in the form of a hick liquid. The thick liquid is filled into cans. A lid is applied, and the container is hermetically sealed. The sealed can is then placed into conventional equipment designed to sterilize the contents. This is usually accomplished by heating to temperatures of greater than about 230° F. for an appropriate time, which is dependent on, for example, the temperature used and the composition.

Compositions of the present invention (particularly foods) can be prepared in a dry form using conventional processes. In one contemplated embodiment, dry ingredients, including, for example, animal protein sources, plant protein sources, grains, etc., are ground and mixed together. Moist or liquid ingredients, including fats, oils, animal protein sources, water, etc., are then added to and mixed with the dry mix. The mixture is then processed into kibbles or similar dry pieces. Kibble is often formed using an extrusion process in which the mixture of dry and wet ingredients is subjected to mechanical work at a high pressure and temperature, and forced through small openings and cut off into kibble by a rotating knife. The wet kibble is then dried and optionally coated with one or more topical coatings which may include, for example, flavors, fats, oils, powders, and the like. Kibble also can be made from the dough using a baking process, rather than extrusion, wherein the dough is placed into a mold before dry-heat processing.

Treats of the present invention can be prepared by, for example, an extrusion or baking process similar to those described above for dry food.

EXAMPLE

The following example is merely illustrative, and not limiting to this disclosure in any way.

Example 1

Twenty four senior dogs were evaluated for initial GFR, weighed, and then assigned to one of three foods. Approximately two weeks prior to the study, all of the dogs were tested for microalbuminuria, had their blood pressure measured, had their GER estimated by serum iohexol clearance, and had a DEXA analysis completed.

The three foods used in the study were a first control food, a second control food, or a dry test food for one year. Control Food 1 was modeled after a nutrient composite of a typical dry dog food in the United States. Control Food 2 was similar to Control Food 1, but phosphorus and calcium were restricted and vitamins E and C were enhanced. The Test Food was similar to Control Foods 1 and 2, but protein, calcium and phosphorus were restricted and vitamins E and C were enhanced.

On Day 1 of the study, the animal subjects had blood drawn and then were fed the appropriate food. Initial weights were recorded and daily food intake was recorded throughout the study. Animals were fed to maintain body weight throughout the year long study.

On or about Day 120 of the study, all animals were vaccinated (all killed vaccine) in a five way lepto vaccine. Approximately two weeks later, blood was drawn from the animals to ascertain vaccination response. The animals were also vaccinated again to ascertain secondary response.

After about six months of the study, GFR of the animals was estimated, a DEX analysis was completed, blood pressure was taken and blood analysis was undertaken. This same set of analyses was performed after about one year from the beginning of the study.

The ingredients in the control foods and test food are described in Table 2 below:

TABLE 2

Compositions of Control and Test Foods

| Ingredient | % by Weight Control Food 1 | % by Weight Control Food 2 | % by Weight Test Food |
|---|---|---|---|
| Corn | 61.128 | 56.659 | 65.992 |
| Chicken by-product meal | 23.68 | 14.843 | 13.70 |
| Animal Fat | 4.24 | 6.52 | 6.80 |
| Soybean mill run | 4.50 | 4.50 | 4.50 |
| Flaxseed |  | 4.00 | 4.00 |
| Corn gluten meal | 1.00 | 9.60 | 1.00 |
| Egg product | 1.00 | 1.00 | 1.00 |
| Palatability enhancer | 1.00 | 1.00 | 1.00 |
| Potassium Chloride | .38 | .69 | .67 |
| Choline Chloride | .27 | .27 | .27 |
| Glyceryl Monostearate | .20 | .20 | .20 |
| Calcium carbonate | .36 | .10 | .16 |
| Salt (NaCl) | .66 | .12 | .16 |
| L-Tryptophan |  | .05 | .05 |
| Taurine |  | .05 | .05 |
| Dicalcium Phosphate | 1.45 |  | .05 |
| L-Lysine HCl |  | .05 | .05 |
| Micronutrient premix | .132 | .348 | .348 |
| Vitamins |  | 0.01–0.2 | 0.01–0.2 |
| Minerals |  | 0.01–0.2 | 0.01–0.2 |
| Vitamin C |  | 100 ppm | 100 ppm |
| Vitamin E | 160 IU/Kg | 750 IU/Kg | 750 IU/Kg |
| Protein % | 25.3 | 25.4 | 19.4 |
| Phosphorus % | 1.0 | .55 | .55 |

The results of his experiment are shown in FIG. 1 and in Table 3, below. As show in FIG. 1, the dogs that were fed the Test Food showed an increase in GFR over the course of the one year of the test. The dogs that were fed Control Food 1, without nutrient restriction and antioxidant enhancement, exhibited a slight increase in GFR, but a significantly lower increase an the dogs that were fed the Test Food. Lastly, dogs that were fed Control Food 2, with phosphorus restriction and enhanced antioxidants, exhibited an increase in GER over the first six months of the study, but then a significant decrease in GFR over the last six months of the study. And, as shown in Table 3, the dogs exhibited a positive correlation of concentration of creatinine and concentration of serum urea nitrogen—as the concentration of creatinine decreased, so did the concentration of serum urea nitrogen. Similarly, the dogs exhibited a positive correlation of concentration of phosphorus and concentration of serum urea nitrogen. Conversely, the dogs exhibited a negative correlation of concentration of serum urea nitrogen and GFR—as serum urea nitrogen decreased, GFR increased.

TABLE 3

Change in Concentrations of Serum Urea Nitrogen Correlate to Specific Blood Metabolites and GFR Test Food

|  | Change in Serum Urea Nitrogen |
|---|---|
| Change in Concentration of Creatinine | 0.68 (P < 0.001) |
| Change in Concentration of Phosphorus | 0.51 (P = 0.002) |
| Change in GFR | −0.40 (P = 0.015) |

All the references cited above are incorporated by reference into this patent.

The words "comprise," "comprises," and "comprising" are to be interpreted inclusively rather than exclusively.

The above detailed description is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

I claim:

1. A method for improving kidney function in an animal with reduced kidney function, the method comprising maintaining the animal on a diet that comprises a food composition comprising 25 to 2000 mg/kg vitamin C and 300 to 2000 IU/kg vitamin E, protein from 14% to 20% (based on dry weight of the composition), and phosphorous in an amount less than 0.50% (based on dry weight of the composition); wherein the animal is maintained on said diet for a time period effective to improve kidney function and to maintain the overall health of the animal.

2. The method of improving the kidney function of an animal of claim 1, wherein the weight ratio of the vitamin C to the Vitamin E is from about 0.2:1 to about 7:1.

3. The method of improving the kidney function of an animal of claim 1, wherein the weight ratio of protein to phosphorous is from about 17:1 to about 110:1.

4. The method of improving the kidney function of an animal of claim 1, wherein the weight ratio of protein to antioxidants is from about 70:1 to about 410:1.

* * * * *